United States Patent [19]

Biricik et al.

[11] Patent Number: 4,866,264

[45] Date of Patent: Sep. 12, 1989

[54] METHOD AND APPARATUS FOR MEASURING NON-RECIPROCAL LOSS OF THIN MAGNETIC FILMS AND MAGNETIC MIRRORS

[75] Inventors: V. Warren Biricik, Palos Verdes Estates; Frank R. Nakatsukasa, Gardena, both of Calif.

[73] Assignee: Northrop Corporation, Hawthorne, Calif.

[21] Appl. No.: 265,390

[22] Filed: Oct. 31, 1988

[51] Int. Cl.[4] ............................ G02F 1/01; G01J 4/00
[52] U.S. Cl. .................................... 250/225; 356/369
[58] Field of Search ............... 250/225; 356/367, 368, 356/369, 370, 445, 447, 350

[56] References Cited

U.S. PATENT DOCUMENTS

| | | | |
|---|---|---|---|
| 3,545,840 | 12/1970 | Ferguson | 356/369 |
| 4,053,232 | 10/1977 | Dill et al. | 250/225 |
| 4,105,338 | 8/1978 | Kuroha | 356/369 |
| 4,265,543 | 5/1981 | Barclay et al. | 356/369 |
| 4,658,148 | 4/1987 | Naito | 250/225 |

OTHER PUBLICATIONS

Lissberger et al., "Automatic Ellipsometry Without a Phase Plate", *J. of Phys. E., Sci. Instrum. (GB)*, vol. 10, No. 6, 6/77, pp. 635–641.
Lentz et al., "Automatic Magneto-Optic Rotation Tester", *J. of Optical Soc. of America*, vol. 51, No. 6, 8/61, pp. 890–894.
Kruszewski et al., "Instrument for the Measurement of Thin Films Parameters by Ellipsometry", *Elektronika*, vol. 16, No. 9 (Poland), 1975, pp. 361–363.
Bebb, "A Polarimetric Method of Measuring Magneto-Optic Coefficients", *IBM J. of Res. and Dev.*, vol. 6, 10/62, pp. 456–461.
Chang et al., "Magnetic Properties Test Instrument", *IBM Tech. Disc. Bull.*, vol. 8, No. 8, 1/66, pp. 1105–1106.
Schneider et al., "Nondestructive Low-Noise Measuring of Magnetic Properties of Magnetic Storage Media", *IBM Tech. Disc. Bull.*, vol. 19, No. 4, 9/76, pp. 1296–1297.
Blyumkina et al., "System for Automating Ellipsometric Measurements", *Opt. Spectrosc.*, vol. 40, No. 3, 3/76, pp. 339–340.

*Primary Examiner*—Edward P. Westin
*Assistant Examiner*—Michael Messinger
*Attorney, Agent, or Firm*—Terry J. Anderson; Robert B. Block

[57] ABSTRACT

Method and apparatus for high accuracy measurement of non-reciprocal reflectivity of magnetic thin film materials and magnetic mirrors. An ellipsometer which employs a Helmholtz coil to supply magneto-optic modulation to p-polarized light and an acousto-optic modulator to provide intensity modulation is utilized in conjunction with a novel scheme of analyzer rotation and computational techniques to accurately measure non-reciprocal reflectivity. A microcomputer is used to provide controlled rotation of polarizing elements, data logging, data analysis, and output. The non-reciprocal reflectivity value is determined by the slope of the measured ratio of magneto-optically modulated and absolute intensities ($\delta I_{magnetic}/I_{total}$), plotted against a function of the analyzer angle $G(\Psi)$.

4 Claims, 3 Drawing Sheets

METHOD AND APPARATUS FOR MEASURING NON-RECIPROCAL LOSS OF THIN MAGNETIC FILMS AND MAGNETIC MIRRORS

BACKGROUND OF THE INVENTION

1. Field of the Invention

The present invention relates to measurement devices, and in particular, to a device which can accurately measure non-reciprocal relectivity of thin film magneto-optic materials and ring laser gyro magnetic mirrors. The use of such a device is required in the manufacture and testing of magneto-optic rate biasing mirrors (magnetic mirrors) used in certain ring laser gyroscopes.

2. Description of the Prior Art

Prior art non-reciprocal reflectivity (the difference between the p-polarized light reflectivities with and without magnetization present) measurement methods and apparatus are, in general, concerned with measurements wherein the non-reciprocal reflectivity values are large (>0.01%). These measured non-reciprocal reflectivity values are used in conjunction with non-reciprocal phase shifts to determine magneto-optic constants of thin film magnetic materials and to predict the performance of thin film magnetic layers in a multilayer optical structure. In optical thin film designs employing magnetic layers and requiring very small non-reciprocal reflectivities (magnetic mirrors employed in ring laser gyroscopes where non-reciprocal reflectivities of less than 0.0001% are desired) the designs are modeled using material constants derived from ellipsometric measurements. Difficulties arise when actual verification of these non-reciprocal reflectivity values are attempted.

An ellipsometric technique which measures the amplitude of modulation of magneto-optic intensity as a function of polarizer angle in a PCSA (polarizer-compensator-sample-analyzer) configuration ellipsometer has been disclosed in the following articles:

(1) H. T. Minden,"Ellipsometric Measurement of the Kerr Magnetooptic Effect," Applied Optics, Vol. 18.p. 813 (1979).

(2) J. H. Kaiser and J. Kranz, "Ellipsometric Measurement of Magnetooptical Nonreciprocal Effects," Applied Physics B, Vol. 39, p. 15 (1986).

(3) J. P. Krumme, V. Doormann, and C. P. Klages, "Measurement of the magnetooptic Properties of Bismuth-Substituted Iron Garnet Films Using Piezobirefringent Modulation," Applied Optics, Vol. 23, p. 1184 (1984).

Analytically, it has been shown by Minden that the magneto-optic intensity modulation is a linear function of a function of the polarizer angle when the analyzer is fixed at the null position. The slope and intercept of normalized magneto-optic intensity, when plotted against a function of the polarizer angle ($\delta I_{mag}/I$ vs $F(\phi)$), are used to define the magneto-optic cons of thin magnetic films as shown below.

For the analyzer fixed at the ellipsometric null position, the modulation of the polarizer angle results in a simplified expression for the depth of modulation of the magneto-optic intensity $$\delta I_{mag}/I = 0.5 \delta R_p +/- F(-/+\phi) \Phi$$

where $F(\phi)$ is only function of the polarizer angle $\phi$ $$F(\phi) = \cos \phi / (1 + \sin \phi)$$

where $\delta R_p$ refers to the non-reciprocal reflection coefficient of p-polarized light and $\delta \Phi$ denotes the non-reciprocal phase shift. Therefore, the depth of modulation of the magneto-optic intensity is a linear function of $F(\phi)$ with a slope equal to dP (non-reciprocal phase shift) and an intercept equal to $\delta R_p/2$ (one half of the non-reciprocal reflectivity). The slope ($\delta \Phi$) of $\delta I_{mag}/I$ vs $F(\phi)$ can be extracted accurately using a least squares fit linear approximation to the measured data. On the other hand, the determination of the intercept requires very accurate absolute measurements of the intensity and is susceptible to measurement noise. In $\delta R_p$ measurements in the 0.0001% range, errors of two orders of magnitude (0.01%) have been observed when using this technique to measure non-reciprocal reflectivities of ring laser gyro magnetic mirrors.

The use of magnetic thin film structures as rate biasing elements in ring laser gyroscopes requires designs having non-reciprocal reflectivity values less than 0.0001%. Therefore, the requirement for a suitable technique for accurately measuring non-reciprocal reflectivities is necessary for the successful development of magnetic mirrors.

SUMMARY OF THE PRESENT INVENTION

The present invention provides an ellipsometric method for the accurate measurement of small non-reciprocal reflectivity values of magnetic thin films and magnetic mirrors.

The ellipsometric magneto-optic characterization technique utilized in the invention is based on the transverse Kerr effect acting on reflection of a p-polarized light beam from thin film structure containing at least one magnetic film (the transverse Kerr effect configuration refers to the case where the electric field is in the plane of incidence and is also perpendicular to the magnetization of the thin film). The present invention utilizes acousto-optic modulation ellipsometry for measuring the complex index of refraction (N=n−i k) of the thin magnetic films. Magneto-optic modulation, in conjunction with acousto-optic modulation, is used to measure the magneto-optic properties ($Q = Q_1 - i Q_2$).

In particular, apparatus comprising a magneto-optic ellipsometer constructed to provide magnetic modulation of th sample under evaluation and acousto-optical modulation of light is utilized to perform an angular can of the analyzer element to specific offset locations around the ellipsometric null while positioning the polarizer at its ellipsometric null. Values of magneto-optic intensity ($\delta I_{mag}$) and total intensity (I) are determined at each point of the analyzer scan. A ratio of these values, ($\delta I_{mag}/I$), is plotted against a newly defined function, $G(\Psi)$, which is related to the angular locations of the analyzer element of the ellipsometer. The slope of the resultant line is the value of the non-reciprocal reflectivity of the sample under examination.

BRIEF DESCRIPTION OF THE DRAWING

For a better understanding of the invention as well as other objects and further features thereof, reference is made to the following description which is to be read in conjunction with the accompanying drawing wherein.

DETAILED DESCRIPTION OF THE PREFERRED EMBODIMENT

Figure 1:
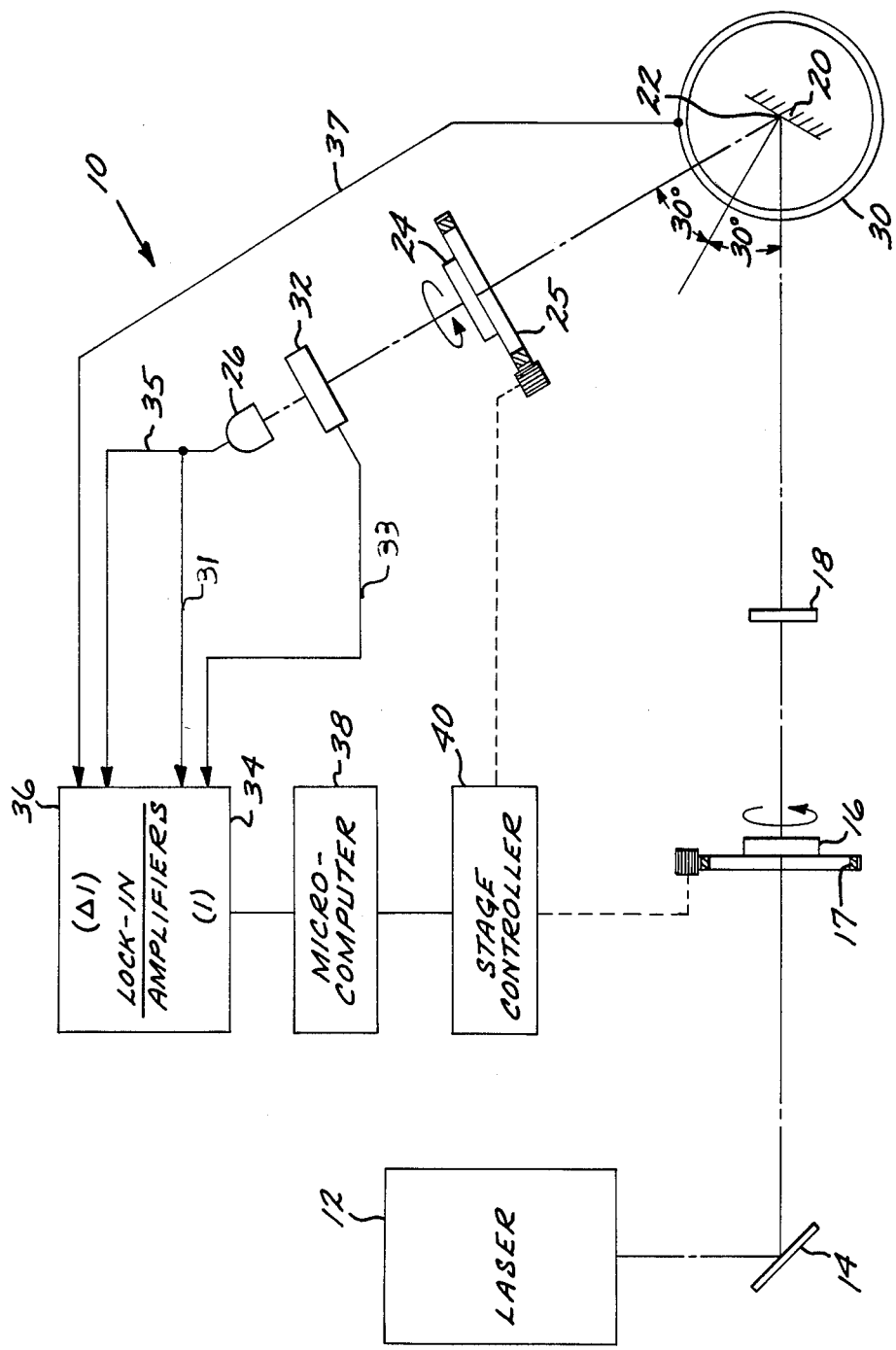
FIG. 1 is a schematic diagram of the apparatus of the present invention.

In order to put the invention in perspective, the following is a discussion of the principles involved which form the basis of the present invention. The following derivation shows that it is possible to accurately measure the non-reciprocal reflectivity of thin magnetic films and optical structures using such films.

The intensity function in a PCSA configuration ellipsometer can be described by the following equation:

$$I = \cos^2 A [(\tan \Psi +/- (\tan A)^2 -/+ 2\tan A \tan\phi(1 -/+ \sin\phi)]$$

where A denotes the analyzer angle and $\phi$ is related to the polarizer angle. The magneto-optic intensity modulation is obtained through the differentiation of the intensity function with respect to the magnetization of the film, i.e., $$\delta I_{mag} = 2\tan\phi \cos^2 A[0.5(\tan\phi + \tan A \sin\phi)\delta R_p + \tan A \cos\phi d\Phi]$$

The precise determination of the non-reciprocal reflectivity can be obtained by modulating the analyzer while the polarizer is kept at the ellipsometric null position. For this case it can be shown from the above expressions that the normalized magneto-optic intensity function can be expressed as $$\delta I_{mag}/I = G(-/+\Psi)\delta R_p$$

where G is a function of the analyzer null and modulated analyzer angles $$G(-/+\Psi) = \tan \Psi / (\tan \Psi +/- \tan A)$$

The magneto-optic intensity expression given above indicates that the non-reciprocal reflectivity is the slope of the magneto-optic intensity modulation. The accurate measurement of non-reciprocal reflectivity requires the modulation of the analyzer angle while the polarizer is set a the null position and calculating the slope of the measured data points by using a least squares fit technique.

Magneto-optic effects manifest themselves as first order perturbations and consequently it is difficult to accurately determine the magneto-optic constants of a given material, the constants being directly related to non-reciprocal reflectivity.

Conventional ellipsometry can be used to determine the optical constants of thin film materials but it is not suitable for the measurement of magneto-optic constants. In addition, the magneto-optic properties of specially designed optical thin film structures, such as ring laser gyroscope magnetic mirrors, have inherently small non-reciprocal reflectivities which evade the capabilities of available instruments due to low sensitivity and noise rejection capabilities.

In accordance with the teachings of the present invention, the following additions to a classical ellipsometer are provided to perform accurate magneto-optic non-reciprocal reflectivity measurements:

(1) Magnetic Modulation: This is accomplished by placing the sample in a suitably modulated magnetic field produced, for example, by an electromagnet, a Helmholtz coil, or a rotating permanent bar magnet, or two pairs of orthogonally disposed conductors (one pair being in a direction perpendicular to the plane of incidence) which are pulse energized to provide coherent rotational switching of the film magnetization. In the special case of a magnetic film having a well defined uniaxial anisotropy, coherent rotational switching or mechanically rotating the film will provide the required magnetic modulation. The fixture is arranged to ensure that the magnetic modulation axis is perpendicular to the plane of incidence of light.

(2) Magneto-Optic Signal Differentiation: This is accomplished by frequency separation of optical and magneto-optical modulation and the use of phase locked detection. This may also be accomplished by measuring the differences in magneto-optic signal amplitudes for the different magnetic orientations.

(3) Magneto-Optic Data Collection and Computation: the ellipsometer is first nulled to determine the angular settings of the polarizer and analyzer. While the polarizer is set at the ellipsometric null angle, the analyzer is modulated around its null point and the ratio of magneto-optic light intensity and total light intensity is measured for each analyzer angle. This ratio is then plotted against a specific function of the analyzer angle $G(\Psi)$ (defined previously). The slope of normalized magneto-optic intensity when plotted against the function $G(\Psi)$ is measured and identified with the non-reciprocal reflectivity.

Referring now to the schematic diagram of FIG. 1, apparatus 10 of the present invention comprises a laser 12, reflecting mirror 14, polarizer 16, quarter wave plate 18, test stand 20, test mirror 22 having a magnetic film component, analyzer 24 and low noise detector 26. The just recited components of apparatus 10 form a conventional PCSA ellipsometer. In accordance with the teachings of the present invention, apparatus 10 further comprises a magnetic modulation means 30, acousto-optic modulator 32, conventional lock-in amplifiers 34 and 36, microcomputer 38 and polarizer and analyzer conventional rotational stage controllers 40. Microcomputer 38 controls the ellipsometer components (polarizer rotational stage, analyzer rotational stage, and magnetic modulation), acquires data in real-time (through lock-in amplifiers 34 and 36), and processes the ellipsometric data providing the measured value of non-reciprocal reflectivity. The apparatus 10 and test stand 20 are configured so as to be able to measure the sample for any value of the angle of incidence of the laser beam (FIG. 1 shows the set-up at 30deg, angle of incidence which is a required for measuring magnetic mirrors utilized in ring laser gyroscopes having a triangular geometry).

Laser 12 generates laser beam 13 and is preferably a helium-neon laser operating at the same wavelength that the ring laser gyroscope using the magnetic mirror operates. Two common wavelengths employed by the invention described herein are 632.8 nm and 1150 nm. The magnetic modulation means 30 preferably Comprises a Helmholtz coil (such as is shown in FIG. 1), although the other means described previously could be utilized instead. Lock-in amplifier 34 synchronizes the measurement of light intensity on lead 31 to a high frequency signal from the acousto-optic modulator 32 on lead 33; lock-in amplifier 36 synchronizes the measurement of magnetically modulated intensity on lead 35 (magneto-optic intensity) to a medium frequency signal from the magnetic modulation means 30 on lead 37. The lock-in amplifiers thus only respond to signals at predetermined, synchronized time periods to minimize the detection of random noise and also provide time-averaged signals to further reduce the effect of noise on the measurement.

The optical polarizer 16 is mounted on a rotational stage controlled by computer 38 via stage controller 40, the stage having a resolution greater than 0.01 degrees. Similarly, analyzer 24 is mounted on a rotational stage 25 controlled by computer 38 via stage controller 40, the stage having a resolution greater than 0.01 degrees. As noted previously, test stand 20 has an external magnetic modulating field which can be switched at frequencies of IKHz by a magnetic driver (not shown), the magnetic field being perpendicular to the plane of incidence of the coherent light beam and in the plane of the magnetic film. Acousto-optic modulator 32 is capable of modulating the light beam incident thereon at frequencies over 10KHz, the control frequency being established by a manual control device (not shown).

Extraction of the non-reciprocal reflectivity requires the measurement of both the magneto-optic intensity ($\delta I_{mag}$) and total intensity (I) as a function of the analyzer angle (P). The expression for $\delta_{Rp}$, as noted hereinabove, is based on determining the ratio ($\delta I_{mag}/I$) accurately. To minimize errors produced by low frequency drift in the measurement apparatus, a dual phase sensitive scheme, which simultaneously modulates both the thin film magnetization and the laser beam intensity to extract ($\delta I_{mag}$) and (I) directly in lock-in amplifiers 34 and 36, is employed.

The microcomputer calculates the ratio of instrumentally averaged intensity values, i.e., typically the $\delta I_{mag}$ and I values represent an average of 100 sequential individual measurements. In this way, low frequency drifts in the laser intensity are effectively averaged out.

In an effort to mitigate against the adverse effects of flicker or l/f noise the modulation frequencies of both the magnetic modulation and laser light have to be raised to kHz regime. In one implementation of the magneto-optically modulated ellipsometer, a Helmholtz coil to modulate the magnetic field is utilized. This coil was specifically designed to provide a 10 Oersted field with a 1 kHz nearly square wave modulated magnetic field. The acousto-optic modulator which provided modulation to the total intensity, was operated around 8 kHz. These noise reduction techniques coupled with the angular modulation of the analyzer have allowed for accurate determination of the magneto-optic non-reciprocal reflectivity produced by thin magnetic films and ring laser gyroscope magnetic mirrors.

In a typical thin magnetic film measurement, opaque permalloy (83Ni/17Fe) films were deposited on glass substrates and measured. Typical measured data on permalloy films is shown in Table 1.

TABLE 1

| Normalized Magneto-Optic Intensity as Function of Analyzer Angle and G ($\Psi$). | | |
|---|---|---|
| P (degree) | G($\Psi$) | $\delta I_{mag}/I$ ($\times 1000$) |
| 33.52 | 6.598 | −1.090 |
| 34.52 | 7.239 | −1.172 |
| 35.52 | 8.039 | −1.353 |
| 36.52 | 9.066 | −1.499 |
| 37.52 | 10.433 | −1.786 |
| 49.52 | −8.558 | 1.483 |
| 50.52 | −7.191 | 1.218 |
| 51.52 | −6.164 | 1.050 |
| 52.52 | −5.364 | 0.902 |
| 53.52 | −4.723 | 0.779 |

Figure 2:
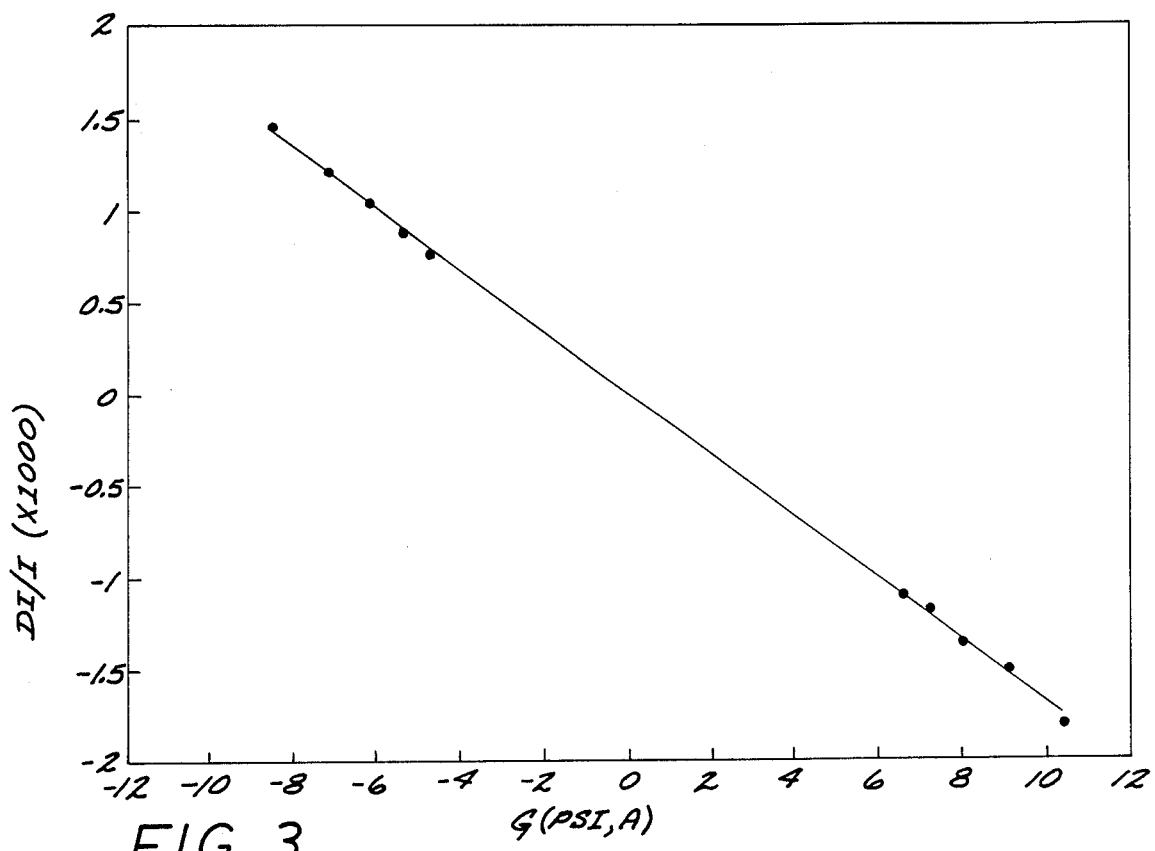
FIG. 2 is a graph showing the variation of the normalized magneto-optic intensity as a specific function of the analyzer angle for a thin permalloy film material.

The data given in Table 1 shows the variation of the normalized magneto-optic intensity as the analyzer is modulated around the null position. These data are plotted in FIG. 2. It is seen from FIG. 2 that the normalized magneto-optic intensity varies linearly as a function of G($\Psi$) as was predicted by theory. From the slope of the normalized magneto-optic intensity function th following non-reciprocal reflectivity value has been calculated for permalloy films a 1150 nm wavelength:

$$\delta R_p = -0.0083\% = -83 \text{ ppm (parts-per-million)}$$

Figure 3:
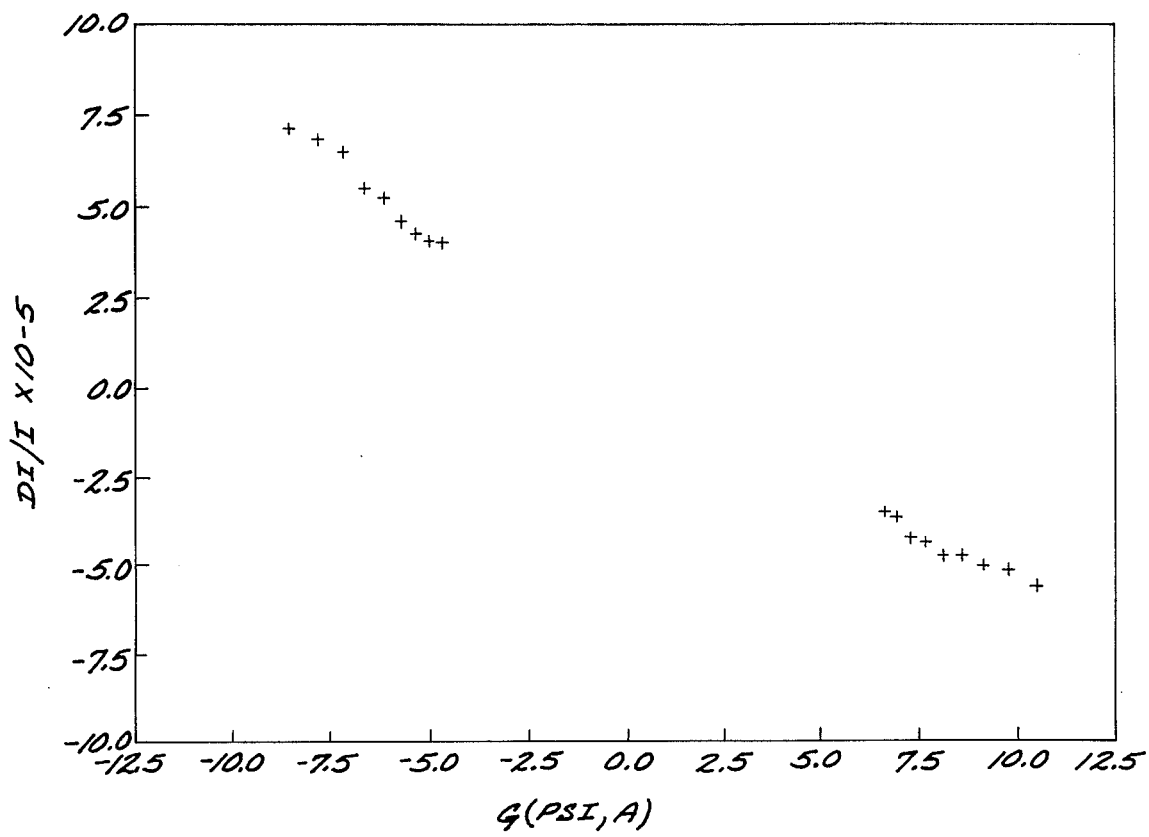
FIG. 3 is the measured value of the normalized magneto-optic intensity as a specified function of the analyzer angle for a ring laser gyroscope magnetic mirror.
Figure 4:
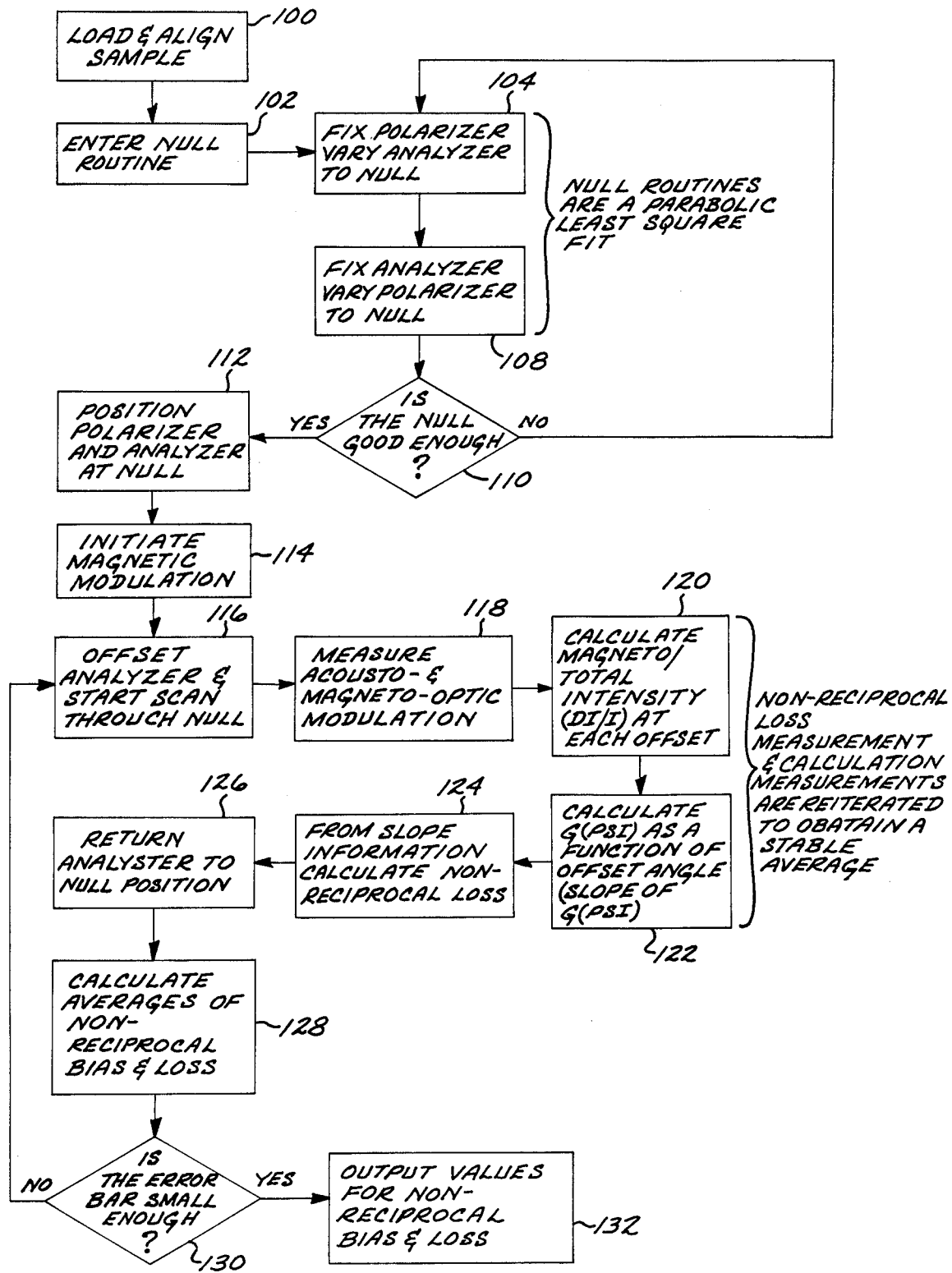
FIG. 4 is a software flow chart utilized to control the apparatus of FIG. 1 and the acquisition and analysis of data.

To further verify the measurement technique, transverse Kerr magnetic mirrors designed for minimum non-reciprocal reflectivity were measured using the magneto-optic ellipsometer described above. Typical data is shown in FIG. 3. The measured non-reciprocal reflectivity value was 6.8 ppm. Utilizing the slope of normalized magneto-optic intensity as a function of G($\Psi$), accurate and repeatable measurements can be obtained with an accuracy of 0.1 ppm. This amounts to an improvement in measurement accuracy of 100 over previous techniques FIG. 4 is a flow chart of the software and is set forth to enable a programmer to program a microcomputer in a manner such that the polarizer and analyzer rotational stage controllers are controlled as disclosed and the appropriate normalized magneto-optic intensity slope (and hence the non-reciprocal reflectivity) calculation is generated. Although most commercially available microcomputers can be used, such as the IBM series of personal computers, an actual embodiment of the invention used an Apple II Plus microcomputer, modified to incorporate an analog to digital converter card.

Symbol 100 represents the beginning of the measurement in which the user loads and aligns the sample to be measured. Symbol 102 represents the data input (initial null position approximations) to the null segment of the program. The routine initially causes the polarizer to be fixed at an approximate null position and the angular position of the analyzer to be varied (symbol 104) until an initial approximation of the analyzer null position is reached; the analyzer is then fixed and the angular position of the polarizer is varied (symbol 108) to an approximation of its null position. The null values are compared to the running average and previous approximations (symbol 110) and if it is less than a maximum acceptable deviation, the analyzer and polarizer are positioned at their respective null angles (symbol 112) of P and A (if the deviation and the null values is greater than the maximum acceptable deviation, the aforementioned process is repeated until the acceptance criteria is satisfied). The magnetic modulation is initiated (symbol 114) and the analyzer is offset (ten degrees or less) from its null position (symbol 116) and scanned through the null angle to an angular location of equal offset on the opposite side of the null. Acousto-optically and magneto-optically modulated intensity values are measured (symbol 118) at each analyzer angle (A). For each setting of the analyzer angle the normalized magneto-optic intensity $\delta I_{mag}/I$ (symbol 120) and the function $G(\Psi)$ (symbol 122) are calculated. The normalized magneto-optic intensity is plotted as a function of $G(\Psi)$ and its slope is calculated (symbol 124) to give the non-reciprocal reflectivity value. The analyzer is then returned to its null position (symbol 126).

The measurements of non-reciprocal reflectivity are reiterated a predetermined number of times to obtain an average value (symbol 128) and a standard deviation. The measured standard deviation is compared with a predetermined allowable error figure (symbol 130); if the error figure is less than the allowable value, the measurement is terminated and the output values of the non-reciprocal reflectivity are printed out (symbol 132); otherwise, the measurements are repeated enough times to minimize the standard deviation of the measured non-reciprocal reflectivity values.

While the invention has been described with reference to its preferred embodiments, it will be understood by those skilled in the art that various changes may be made and equivalents may be substituted for elements thereof without departing form the true spirit and scope of the invention. In addition, many modifications may be made to adapt a particular situation or material to the teaching of the invention without departing from its essential teachings.

What is claimed is:

1. A magnetically and acousto-optically modulated transverse Kerr effect ellipsometer for the measurement of the non-reciprocal reflectivity of a magnetic member comprising:
   a source of coherent radiation for generating a coherent light beam;
   an optical polarizer mounted on a computer controlled rotational member and responsive to said coherent beam;
   a holder for said magnetic member;
   means for generating an external magnetic modulating field which is switched at predetermined frequencies, said magnetic field being perpendicular to the plane of incidence of said coherent light beam and in the plane of the magnetic member.
   an analyzer mounted on a computer controlled rotational member, and responsive to the light beam reflected from said magnetic member;
   an acousto-optic modulator for modulating the light beam transmitted through said analyzer;
   a detector for measuring the light intensity transmitted through said modulator;
   phase sensitive detection means responsive to signals from said acousto-optic modulator and said magnetic field generating means; and
   computer means for setting said polarizer at its null angle and modulating said analyzer around the null angle, measuring at each analyzer angle location both the magneto-optic and total intensities; said computer means also calculating the ratio of the magneto-optic and total intensities ($\delta I_{mag}/I$) as a function of $G(\Psi)$ defined by $$G(\Psi) = \tan \Psi / (\tan \Psi - \tan A_{null})$$

wherein $\Psi$ is the analyzer angle, $A_{null}$ is the null angle of the analyzer; and measuring the slope of the calculation, the measured slope comprising the non-reciprocal reflectivity.

2. The ellipsometer of claim 1 wherein the magnetic modulation means is an Helmholtz coil whose axis is perpendicular to the plane of incidence.

3. The ellipsometer of claim 1 wherein said acousto-optic modulator modulates said light beam at a frequency substantially higher than the magneto-optic modulation.

4. A method for measuring a thin magnetic member comprising the steps of:
   generating a beam of coherent radiation and directing the radiation beam to first an optical polarizer mounted on a computer controlled rotational stage and then a quarterwave plate;
   providing an external magnetic modulating field perpendicular to the plane of incidence of coherent light beam and in the plane of the magnetic member for modulating said magnetic member;
   directing the light output from said magnetic member to an analyzer mounted to a computer controlled rotational member;
   providing an acousto-optic modulator for modulating the output light beam from said analyzer;
   measuring the light intensity of the output from said acousto-optic modulator;
   amplifying the measured light intensity in a manner to reduce the effects of noise on the measurement;
   setting the polarizer at its null angle and modulating the analyzer around the null angle;
   measuring at each analyzer angle location both the magneto-optic and total intensities;
   calculating the ratio of the magneto-optic intensity and the total intensity as a function of $G(\Psi)$ defined by $$G(\Psi) = \tan \Psi / (\tan \Psi - \tan A_{null})$$

wherein $\Psi$ is the analyzer angle, $A_{null}$ is the null angle of the analyzer; and measuring the slope of the calculation, the measured slope being equal to the non-reciprocal reflectivity of the magnetic member.

* * * * *